United States Patent
Jung

(10) Patent No.: US 6,222,061 B1
(45) Date of Patent: Apr. 24, 2001

(54) 2-ALKYL-2-ADAMANTYL 5-NORBORNENE-2-CARBOXYLATES AND METHOD OF PRODUCING THE SAME

(75) Inventor: Hyun-jin Jung, Seoul (KR)

(73) Assignee: Chem Search Corp., Seoul (KR)

( * ) Notice: Subject to any disclaimer, the term of this patent is extended or adjusted under 35 U.S.C. 154(b) by 0 days.

(21) Appl. No.: 09/516,612

(22) Filed: Mar. 1, 2000

(30) Foreign Application Priority Data

Feb. 19, 2000 (KR) .................................. 00-8034

(51) Int. Cl.$^7$ .................................. C07C 69/74
(52) U.S. Cl. .................................. 560/120
(58) Field of Search .............................. 560/120

(56) References Cited

U.S. PATENT DOCUMENTS

| | | | |
|---|---|---|---|
| 4,200,588 | * | 4/1980 | Lednicer et al. ............... 260/571 |
| 6,147,249 | * | 11/2000 | Watanabe et al. .............. 560/120 |
| 6,153,785 | * | 11/2000 | Jung et al. ................... 560/120 |

* cited by examiner

Primary Examiner—Gary Geist
Assistant Examiner—Hector M. Reyes
(74) Attorney, Agent, or Firm—Reed Smith Hazel & Thomas LLP

(57) ABSTRACT

A novel norbornene carboxylate compound and a method of producing the same are provided. The norbornene carboxylate compound is 2-alkyl-2-adamantyl 5-norbornene-2-carboxylate represented by formula (1):

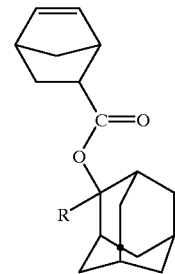

wherein R is methyl or ethyl.

5 Claims, 2 Drawing Sheets

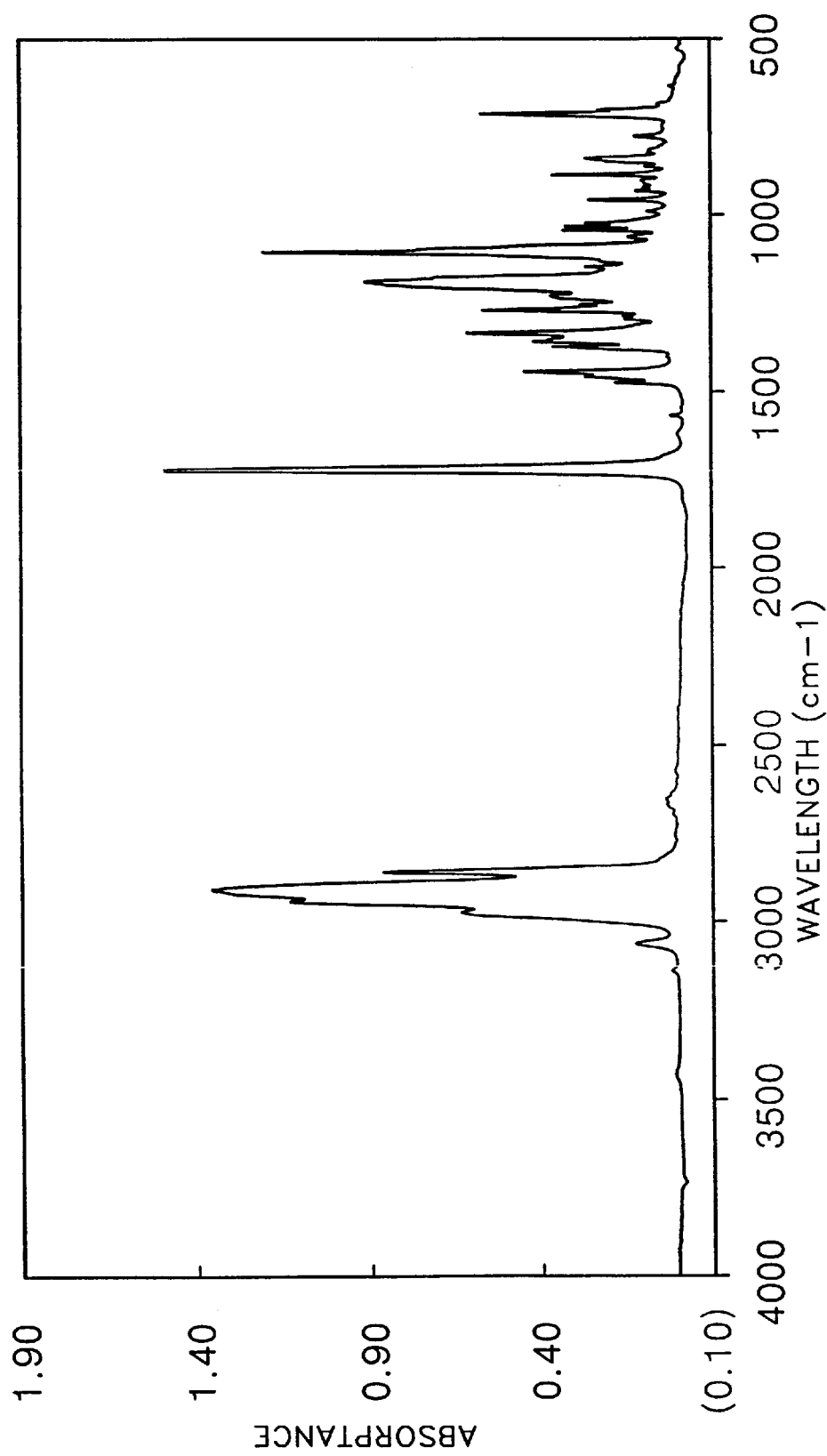

2-ALKYL-2-ADAMANTYL 5-NORBORNENE-2-CARBOXYLATES AND METHOD OF PRODUCING THE SAME

BACKGROUND OF THE INVENTION

1. Field of the Invention

The present invention relates to a novel norbornene carboxylate compound and a method of producing the same, and more particularly, to 2-alkyl-2-adamantyl 5-norbornene-2-carboxylates and a method of producing the same.

2. Description of the Related Art

Norbornene, which is a common name for bicyclo[2.2.1]-2-heptene, is an alicyclic hydrocarbon compound and is widely used in various chemical reactions due to high reactivity of cyclo-double bonds. Specifically, in a norbornene carboxylate compound having a carboxyl group introduced to norbornene, the norbornene can be easily replaced by a bulky substituent. In particular, a bulky substituent containing an alicyclic compound which has low chemical reactivity is in wide use commercially.

Norbornene compounds having a bulky alicylic substitute are commercially used as various flame retardants. Furthermore, the norbornene compound having a bulky alicyclic substituent is capable of copolymerizing with existing monomers to then be used as a polymer flame retardant. Thus, much attention is being paid to the production of norbornene compounds having a bulky alicyclic substituent.

However, conventional norbornene carboxylate compounds having a bulky alicyclic substituent are cumbersome in view of reaction conditions, resulting in poor yield, and the purification thereof is difficult. Thus, it is quite difficult to produce the conventional norbornene carboxylate compounds on a commercial scale.

SUMMARY OF THE INVENTION

To solve the above problems, it is an object of the present invention to provide a norbornene carboxylate compound which can be produced and purified by a simplified process to be suitable for commercial-scale production.

It is another object of the present invention to provide a method for producing the norbornene carboxylate compound.

Accordingly, to achieve the first object, there is provided 2-alkyl-2-adamantyl 5-norbornene-2-carboxylate represented by formula (1):

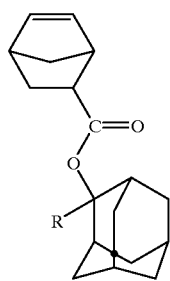

wherein R is methyl or ethyl.

To achieve the second objective, there is provided a method of producing the compound recited in claim 1, including the steps of a) synthesizing 2-alkyl-2-adamantanol having an alkyl group at its own 2-position by reacting 2-adamantanone with either an alkyl Grignard reagent or an alkyl lithium reagent, b) synthesizing 2-alkyl-2-adamantyl acrylate by reacting the 2-alkyl-2-adamantanol synthesized in the step a) with acryloyl chloride, and c) applying the 2-alkyl-2-adamantyl acrylate synthesized in the step b) and cyclopentadiene to Diels-Alder reaction.

Preferably, the Grignard reagent is either alkyl magnesium bromide or alkyl magnesium chloride.

More preferably, if the alkyl is methyl, either methyl magnesium bromide or methyl magnesium chloride is used as the Grignard reagent, and if the alkyl is ethyl, ethyl lithium reagent is used.

In the production method of the norbornene compound according to the present invention, a separation process may be performed after each step is completed. However, the separation process may be performed after all steps are performed in situ.

BRIEF DESCRIPTION OF THE DRAWINGS

The above objects and advantages of the present invention will become more apparent by describing in detail a preferred embodiment thereof with reference to the attached drawings in which:

FIG. 2 is an FT-IR spectrum of 2-methyl-2-adamantyl 5-norbornene-2-carboxylate produced in Example 1 of the present invention.

DESCRIPTION OF THE PREFERRED EMBODIMENTS

Figure 1:
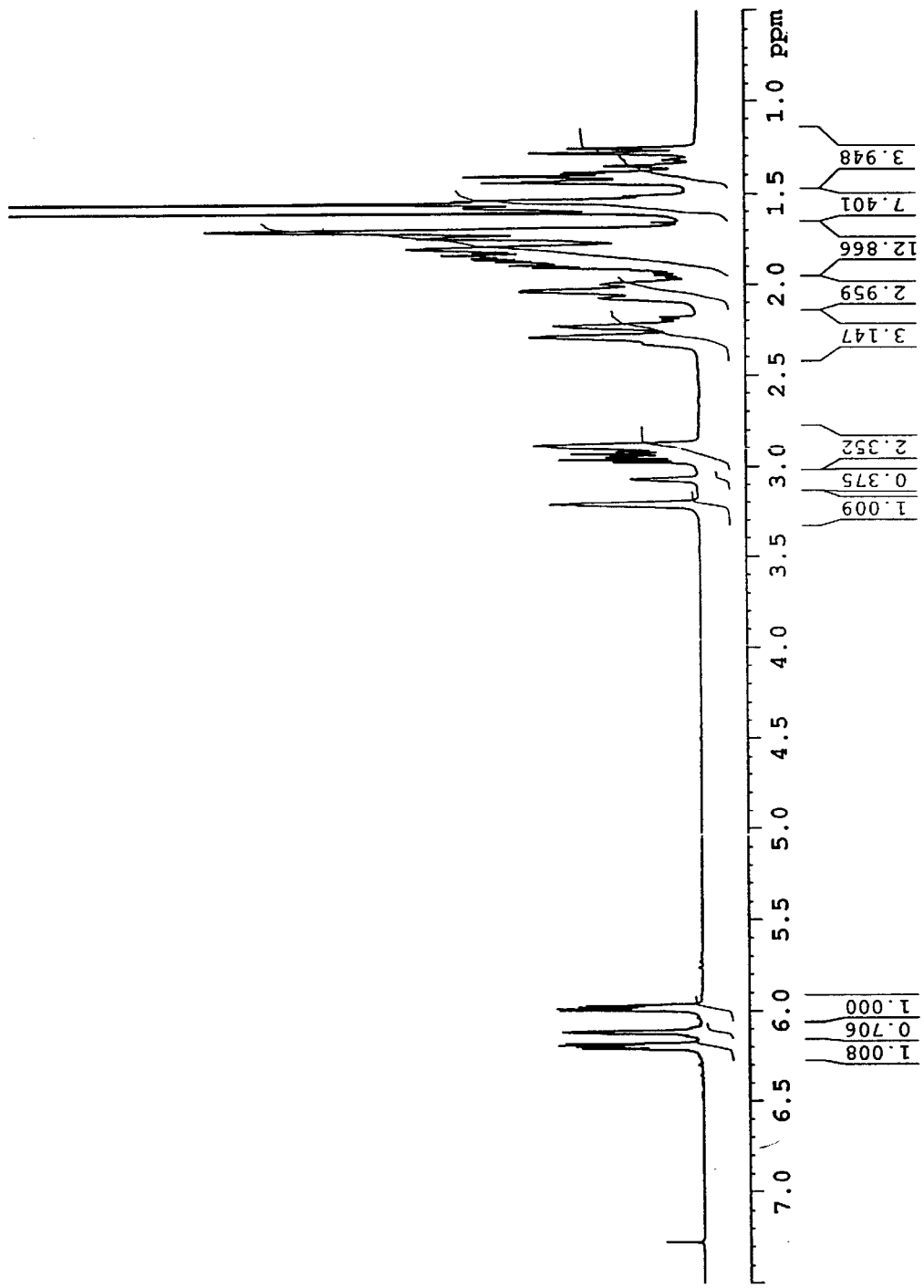
FIG. 1 is an NMR spectrum of 2-methyl-2-adamantyl 5-norbornene-2-carboxylate produced in Example 1 of the present invention.

A process for producing 2-alkyl-2-adamantyl 5-norbornene-2-carboxylate according to the present invention will now be described in detail.

As shown in the following reaction scheme (1), 2-adamantanone and an alkyl Grignard reagent or an alkyl lithium reagent are reacted to synthesize 2-alkyl-2-adamantanol having an alkyl group introduced to a 2-position of 2-adamantanone.

[Reaction scheme (1)]

wherein R is methyl or ethyl, and X is Cl or Br.

In view of side reaction inhibition and reaction yield, if 2-methyl-2-adamantyl 5-norbornene-2-carboxylate is a desired compound, a Grignard reagent is preferably used. If 2-ethyl-2-adamantyl 5-norbornene-2-carboxylate is a desired compound, ethyl lithium reagent is preferably used.

Since the above-described reaction is carried out by a general Grignard reaction mechanism, the reaction temperature and pressure are meaningless in the present invention.

Next, as shown in the following reaction scheme (2), 2-adamantanone having an alkyl group introduced into its own 2-position and acryloyl chloride are reacted to synthesize 2-alkyl-2-adamantyl acrylate.

[Reaction scheme (2)]

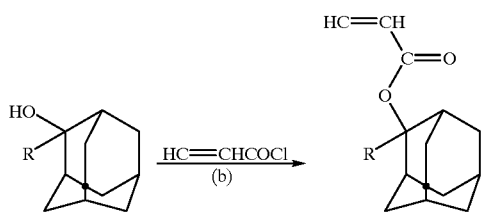

wherein R is the same as defined above.

Finally, as shown in the following reaction scheme (3), a norbornene substitute is prepared by the Diels-Alder reaction of 2-alkyl-2-adamantyl acrylate and cyclopentadiene, thereby obtaining 2-alkyl-2-adamantyl 5-norbornene-2-carboxylate.

[Reaction Scheme (3)]

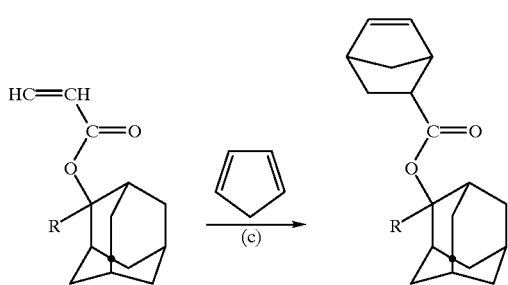

wherein R is the same as defined above.

The present invention is described in more detail below by referring to the following examples, and the examples are intended to illustrate but not limit the invention.

EXAMPLE 1

2-methyl-2-adamantyl 5-norbornene-2-carboxylate a. Synthesis of 2-methyl-2-adamantanol 110 ml of a solution of methyl magnesium bromide (3.0 M) in diethyl ether was diluted with 100 ml of anhydrous tetrahydrofuran (THF). Then, the solution was put into a 1 liter flask and then maintained at 0° C. 2-adamantanone (45 g, 0.3 mol) was dropped slowly using a dropping funnel and then the reaction was stirred at room temperature for about 12 hours. After completion of the reaction, excess THF was removed using a rotary evaporator and then the resultant product was poured into water. Then, the resultant product was neutralized with dilute sulfuric acid and extracted using diethyl ether and was then dried over magnesium sulfate. The obtained crude product was recrystallized using n-hexane and a methylene chloride cosolvent to yield the desired product 2-methyl-2-adamantanol (yield: 80%).

b. Synthesis of 2-methyl-2-adamantyl acrylate 2-methyl-2-adamantanol (33 g, 0.2 mol) and triethylamine (0.22 mol) were dissolved in 300 ml of THF and then acryloyl chloride (19 g, 0.21 mol) was added slowly thereto using a dropping funnel. Then, the reaction was stirred at room temperature for about 12 hours. After completion of the reaction, excess THF was removed using a rotary evaporator and then the resultant product was poured into water. Then, the resultant product was neutralized with dilute sulfuric acid and extracted using diethyl ether and was then dried over magnesium sulfate. The diethyl ether removed crude product was vacuum-distilled to yield the desired product (yield: 80%).

$^1$H-NMR (CDCl$_3$; ppm): 6.3 (doublet), 6.1 (1H, dd), 5.7 (1H, d), 2.3 (2H, s), 1.5–2.1 (m) FT-IR (NaCl; cm$^{-1}$): 2911, 2861, 1718, 1635, 1618, 1401, 1201 c. Synthesis of 2-methyl-2-adamantyl 5-norbornene-2-carboxylate 20 2-methyl-2-adamantyl acrylate (44 g, 0.2 mol) was dissolved in 250 ml of THF, cyclopentadiene (20 g, 0.3 mol) was added slowly thereto at 0° C. and then the reaction temperature was raised to about 50° C. Then, the reaction was stirred for about 20 hours. After completion of the reaction, excess THF was removed using a rotary evaporator and then neutralized with dilute sulfuric acid. Then, the resultant product was extracted using diethyl ether and dried over magnesium sulfate. The obtained crude product was vacuum-distilled to yield the desired compound of viscous colorless liquid (yield: 90%) FIGS. 1 and 2 are NMR and FT-IR spectrums of the compound.

$^1$H-NMR (CDCl$_3$; ppm): 6.2 (1H, m), 6.1 (1H, s), 5.9 (1H, m), 3.2 (1H, s), 2.9 (2H, m), 2.3–1.2 (m) FT-IR (NaCl; cm$^{-1}$): 2910, 2861, 1725, 1334, 1270, 1189, 713

EXAMPLE 2

2-ethyl-2-adamantyl 5-norbornene-2-carboxylate

The title compound was prepared in the same manner as in Example 1, except that an ethyl lithium reagent was used instead of 3.0 M diethyl ether solution of methyl magnesium bromide (yield: 65%).

2-alkyl-2-adamantyl 5-norbornene-2-carboxylate according to the present invention can be produced in a high yield by a simple process and is advantageous for mass production of a commercial scale. A norbornene compound having a bulky substituent can be commercially used as various kinds of flame retardants and is capable of copolymerizing with existing monomers to be used as polymer flame retardants. Further, the norbornene compound can be useful in various applications which require the intrinsic reactivity of norbornene itself.

What is claimed is:

1. 2-alkyl-2-adamantyl 5-norbornene-2-carboxylate represented by formula (1):

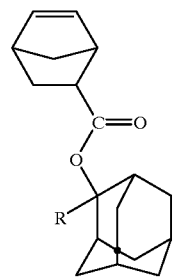

wherein R is methyl or ethyl.

2. A method of producing the compound recited in claim 1, comprising the steps of:

a) synthesizing 2-alkyl-2-adamantanol having an alkyl group at its own 2-position by reacting 2-adamantanone with either an alkyl Grignard reagent or an alkyl lithium reagent;

b) synthesizing 2-alkyl-2-adamantyl acrylate by reacting the 2-alkyl-2-adamantanol synthesized in the step a) with acryloyl chloride; and c) applying the 2-alkyl-2-adamantyl acrylate synthesized in the step b) and cyclopentadiene to Diels-Alder reaction.

3. The method according to claim 2, wherein the Grignard reagent is either alkyl magnesium bromide or alkyl magnesium chloride.

4. The method according to claim 2, wherein if the alkyl is methyl, either methyl magnesium bromide or methyl magnesium chloride is used as the Grignard reagent.

5. The method according to claim 2, wherein if the alkyl is ethyl, ethyl lithium reagent is used.

* * * * *